United States Patent [19]

VandenBerg

[11] Patent Number: Plant 7,463

[45] Date of Patent: Mar. 5, 1991

[54] CHRYSANTHEMUM PLANT NAMED COQUETA

[75] Inventor: Cornelis P. VandenBerg, Salinas, Calif.

[73] Assignee: Yoder Brothers, Inc., Barberton, Ohio

[21] Appl. No.: 409,634

[22] Filed: Sep. 18, 1989

[51] Int. Cl.[5] ..... A01H 5/00

[52] U.S. Cl. ..... Plt./76

[58] Field of Search ..... Plt./75, 76, 77, 78

*Primary Examiner*—Howard J. Locker

*Attorney, Agent, or Firm*—Foley & Lardner, Schwartz, Jeffery, Schwaab, Mack, Blumenthal & Evans

[57] ABSTRACT

A Chrysanthemum plant named Coqueta particularly characterized by its flat capitulum form; pompon capitulum type; tricolored capitulum color of white-yellow-brown; diameter across face of capitulum of up to 4 cm at maturity; uniform eight week photoperiodic flowering response to short days; peduncle length ranging from 6 to 18 cm on open, terminal sprays; tall plant height when grown as a single stem spray cut mum; and excellent tolerance to low temperatures for bud initiation and flower development.

3 Drawing Sheets

The present invention comprises a new and distinct cultivar of Chrysanthemum, botanically known as *Dendranthema grandiflora*, and referred to by the cultivar name Coqueta.

Coqueta, identified as 85-880002, was originated from a cross made by Cornelis P. VandenBerg in a controlled breeding program in Salinas, Calif., in 1984.

The female parent of Coqueta was the cultivar identified as Pinocchio, an unpatented cultivar. Pinocchio is a cut spray mum with a white ray floret color, pompon capitulum type, nine week photoperiodic flowering response to short days, and short plant height. The male parent of Coqueta was an unnamed seedling identified as 79-C08001. The male parent is also a cut spray mum having bronze ray floret color, small decorative capitulum type, nine week photoperiodic flowering response to short days, and tall plant height.

Coqueta was discovered and selected as one flowering plant within the progeny of the stated cross by Cornelis P. VandenBerg in September of 1985, in a controlled environment in Salinas, Calif.

The first act of asexual reproduction of Coqueta was accomplished when vegetative cuttings were taken from the initial selection in November, 1985 in a controlled environment in Salinas, Calif., by technicians working under formulations established and supervised by Cornelis P. VandenBerg.

Horticultural examination of controlled flowerings of successive plantings has shown that the unique combination of characteristics as herein disclosed for Coqueta are firmly fixed and are retained through successive generations of asexual reproduction.

Coqueta has not been observed under all possible environmental conditions. The phenotype may vary significantly with variations in environment such as temperature, light intensity and daylength.

The following observations, measurements and comparisons describe plants grown in Salinas, Calif. under greenhouse conditions which approximate those generally used in commercial greenhouse practice. The low temperature tolerance was determined in repeated flowerings in Bogota, Colombia.

The following traits have been repeatedly observed and are determined to be basic characteristics of Coqueta, which, in combination, distinguish this chrysanthemum as a new and distinct cultivar:

1. Flat capitulum form.
2. Pompon capitulum type.
3. Tricolored capitulum color of white-yellow-brown.
4. Diameter across face of capitulum up to 4 cm at maturity.
5. Uniform eight week photoperiodic flowering response to short days.
6. Peduncle length ranging from 6 to 18 cm on open terminal sprays.
7. Tall plant height, requiring seven long days prior to short days to attain a flowered plant height of 90 to 100 cm for year-round flowerings.
8. Excellent tolerance to low temperatures for bud initiation and flower development.

The accompanying photographic drawings show typical inflorescence and leaf characteristics of Coqueta, with the colors being as nearly true as possible with illustrations of this type.

Sheet 1 is a color photograph of Coqueta grown as a single stem cut spray mum. Sheet 2 is a black and white photograph of three views of the inflorescence of Coqueta. Sheet 3 is a black and white photograph showing the upper and under sides of the leaves of Coqueta at three stages of development (mature, intermediate and immature).

Of the commercial cultivars known to the inventor, the most similar in comparison to Coqueta is the cultivar Moda, disclosed in U.S. Plant Pat. No. 6,886. Reference is made to attached Chart A, which compares certain characteristics of Coqueta to the same characteristics of Moda.

Similar traits are capitulum form and type, spray formation, diameter across face of capitulum and flowering response. Coqueta has a unique tricolored flower color, with the outside white, changing to yellow towards the center and a drak brown dot in the center. Moda is yellow. Coqueta has longer peduncles and more vigor than Moda.

In the following description color references are made to the Royal Horticultural Society Colour Chart.

The color values were determined on plant material grown in Salinas, Calif. on Oct. 12, 1987.

Classification:

*Botanical.*—*Dendranthema grandiflora* cv. Coqueta.

*Commercial.*—Pompon cut spray mum.

INFLORESCENCE

A. Capitulum:

*Form.*—Flat.

*Type.*—Pompon.

*Diameter across face.*—Up to 4 cm at maturity.

B. Corolla of ray florets:

*Color (general tonality from a distance of three meters).*—Yellow.

*Color (under surface).*—Tricolored white-yellow-brown. Outer unfolded petals 155D with a slight margin of 9D. Unfolded petals toward the center of the flower closest to 9C to 9D. Center of the flower has a unique brown dot, closest to 175C.

*Color (under surface).*—4D.

*Shape.*—Straight, concave.

C. Corolla of disc florets:

*Color (mature).*—Closest to 5A, overlaid with 175C.

*Color (immature).*—Closest to 175C.

D. Reproductive organs:

*Androecium.*—Present on disc florets only; scant pollen.

*Gynoecium.*—Present on both ray and disc florets.

PLANT

A. General appearance:

*Height.*—Tall; 90 to 100 cm as a single stem cut mum with 7 long days prior to short days.

B. Foliage:

*Color (upper surface).*—147A.

*Color (under surface).*—147B.

*Shape.*—Deeply lobed, serrated.

CHART A

COMPARISON OF COQUETA AND MODA

| | COQUETA | MODA |
|---|---|---|
| Ray Floret Color | White-Yellow Brown | Yellow |
| Capitulum Form and Type | Flat pompon | Flat pompon |
| Spray formation | Terminal | Teminal |
| Peduncle length | 6 to 18 cm | 5 to 10 cm |
| Diameter Across Face of Capitulum | Up to 4 cm | Up to 4 cm |
| Plant Height | Tall | Short |
| Flowering response period | 8 weeks | 8 weeks |

Comparisons Made of Plants Grown As Single Stem Spray Cut Mums In Salinas, California

I claim:

1. A new and distinct Chrysanthemum plant named Coqueta, as described and illustrated.

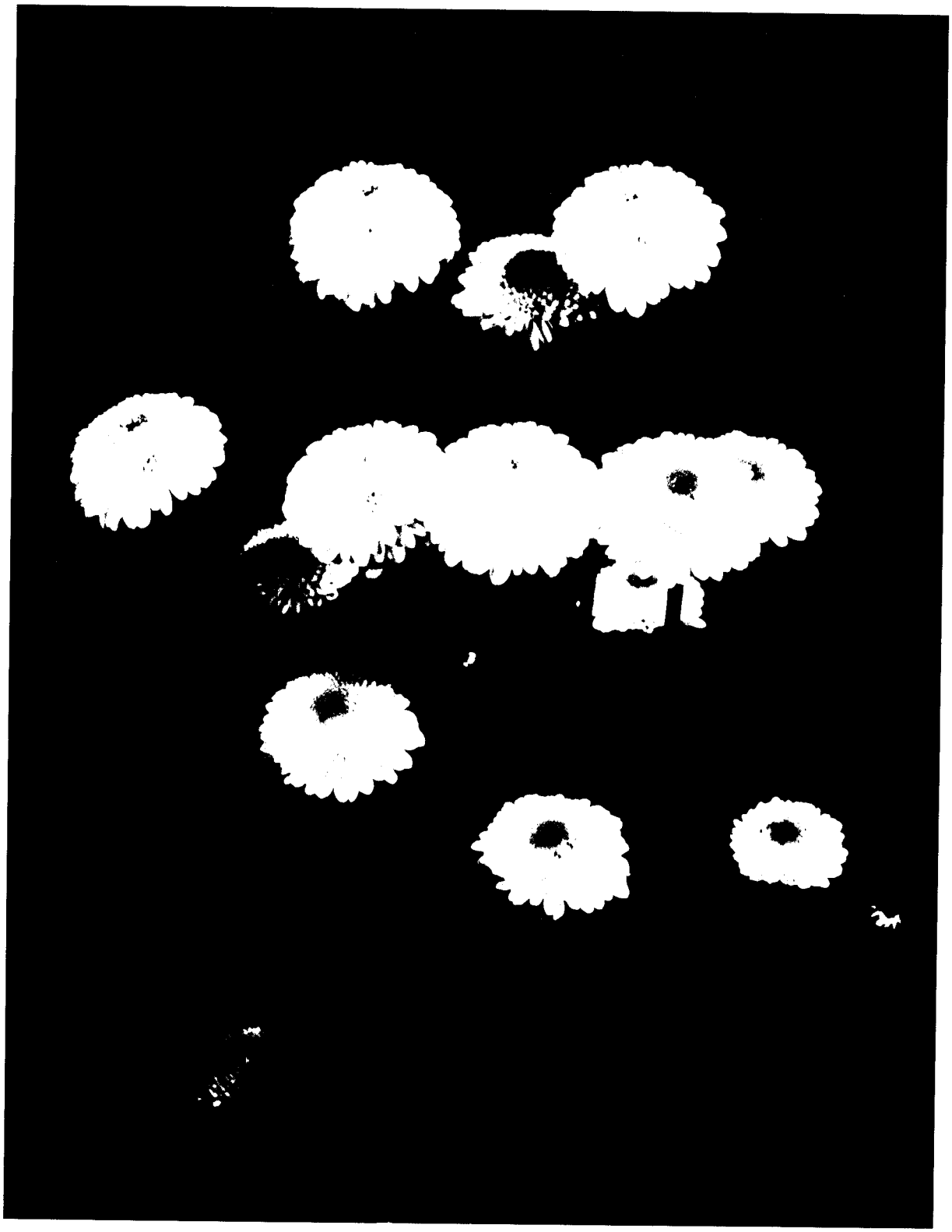

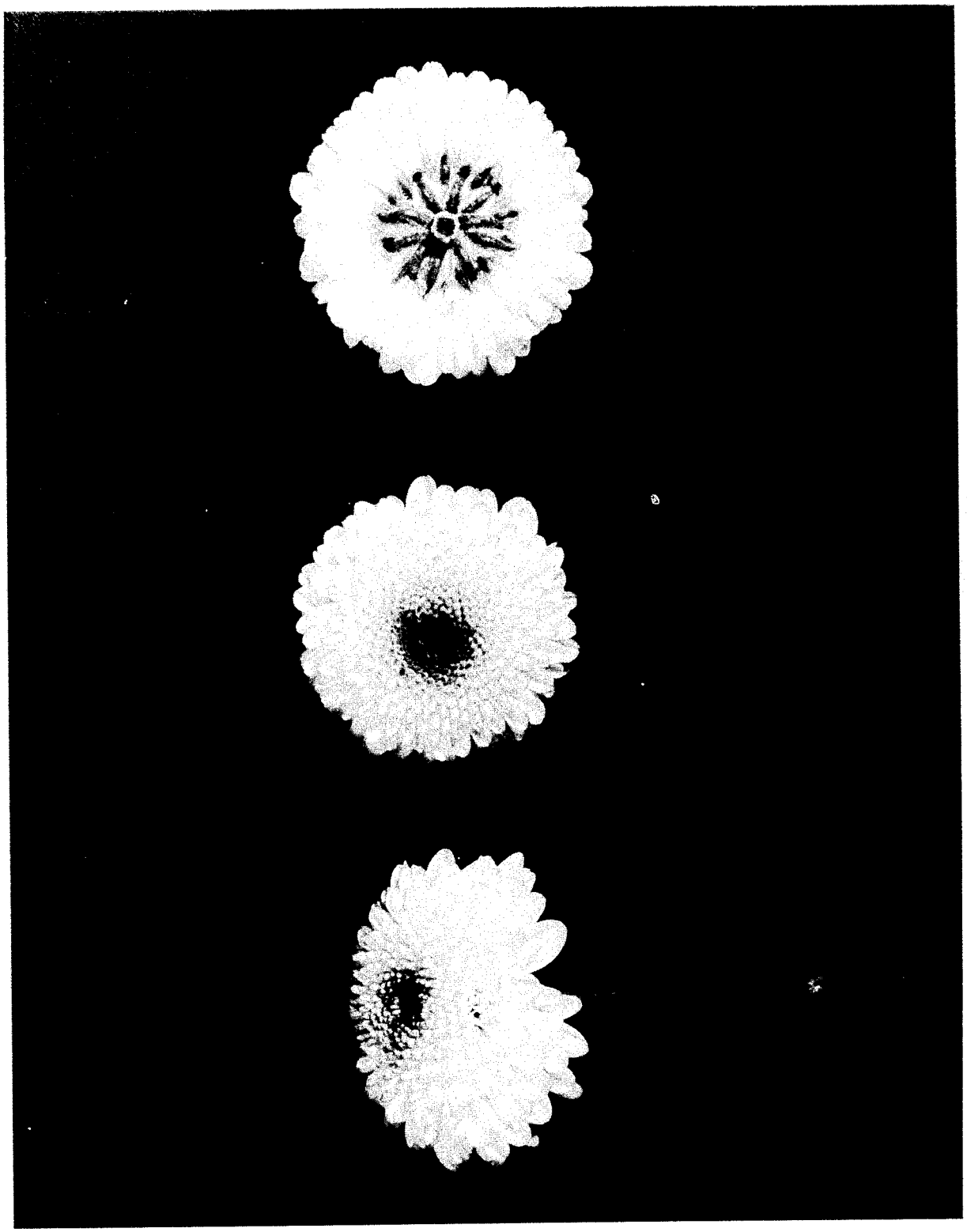

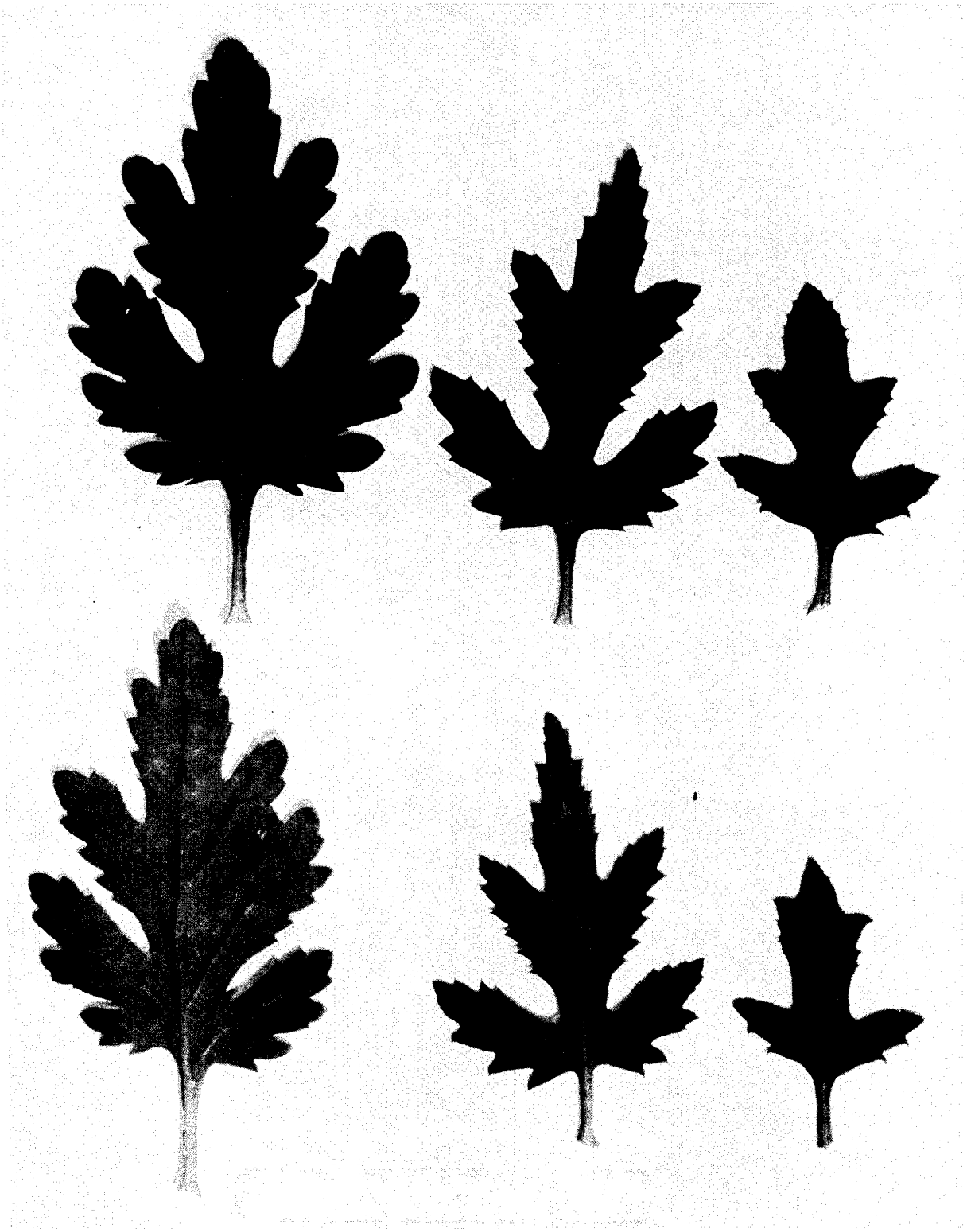

* * * * *